US012807565B2

(12) United States Patent
Schmidt et al.

(10) Patent No.: US 12,807,565 B2
(45) Date of Patent: Nov. 24, 2026

(54) PROCESS FOR MANUFACTURE OF A COMPLEXING AGENT

(71) Applicant: BASF SE, Ludwigshafen (DE)

(72) Inventors: Thomas Schmidt, Ludwigshafen (DE); Armin Stamm, Ludwigshafen (DE); Dan-Tam Daniel Tang, Ludwigshafen (DE); Nataliia Shymanska, Ludwigshafen (DE); Verena Mormul, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 1066 days.

(21) Appl. No.: 17/908,819

(22) PCT Filed: Feb. 25, 2021

(86) PCT No.: PCT/EP2021/054723

§ 371 (c)(1),
(2) Date: Sep. 1, 2022

(87) PCT Pub. No.: WO2021/175701

PCT Pub. Date: Sep. 10, 2021

(65) Prior Publication Data

US 2023/0135390 A1 May 4, 2023

(30) Foreign Application Priority Data

Mar. 3, 2020 (EP) .................................... 20160695

(51) Int. Cl.

| | |
|---|---|
| ***C07C 253/10*** | (2006.01) |
| ***C07C 227/18*** | (2006.01) |
| ***C07C 227/26*** | (2006.01) |
| ***C07C 227/36*** | (2006.01) |
| ***C07C 253/00*** | (2006.01) |
| ***C07C 253/06*** | (2006.01) |

(52) U.S. Cl.

CPC .......... *C07C 253/10* (2013.01); *C07C 227/18* (2013.01); *C07C 227/26* (2013.01); *C07C 227/36* (2013.01); *C07C 253/00* (2013.01); *C07C 253/06* (2013.01); *C07B 2200/07* (2013.01)

(58) Field of Classification Search

CPC ... C07C 253/10; C07C 227/18; C07C 253/00; C07C 253/06; C07C 227/36; C07C 227/26; C07B 2200/07

See application file for complete search history.

(56) References Cited

U.S. PATENT DOCUMENTS

| | | | | |
|---|---|---|---|---|
| 9,802,884 | B2 * | 10/2017 | Reinoso Garcia .... | C07C 227/36 |
| 9,873,659 | B2 * | 1/2018 | Reinoso Garcia ....... | C11D 3/33 |
| 10,619,125 | B2 * | 4/2020 | Franzke ................ | C07C 253/00 |
| 10,676,700 | B2 * | 6/2020 | Schmidt ................ | C07C 227/26 |

FOREIGN PATENT DOCUMENTS

| | | | |
|---|---|---|---|
| NO | 2016/058875 | A1 | 4/2016 |
| WO | 2016/102494 | A1 | 6/2016 |
| WO | 2019/002022 | A1 | 1/2019 |

OTHER PUBLICATIONS

European Search Report for EP Patent Application No. 20160695.1, Issued on Sep. 21, 2020, 3 pages.
International Search Report for PCT Patent Application No. PCT/EP2021/054723, Issued on May 28, 2021, 3 pages.

* cited by examiner

*Primary Examiner* — Laura L Stockton
(74) *Attorney, Agent, or Firm* — ArentFox Schiff LLP

(57) ABSTRACT

A process for making a complexing agent with an enantiomeric excess of at least 60%, wherein said process comprises the following steps:

(a) reacting an aqueous slurry of alanine with an enantiomeric excess of at least 60% with formaldehyde and hydrocyanic acid, thereby forming an aqueous solution of alanine-bisacetonitrile, (b) saponifying the alanine-bisacetonitrile from step (a) by combining the aqueous solution obtained in step (a) with an aqueous solution of alkali metal hydroxide.

7 Claims, No Drawings

PROCESS FOR MANUFACTURE OF A COMPLEXING AGENT

CROSS-REFERENCE TO RELATED APPLICATIONS

This application is a National Stage Entry of PCT/EP2021/054723, filed Feb. 25, 2021, which claims priority to European application No. 20160695.1, filed Mar. 3, 2020, the disclosures of each of which are hereby incorporated by reference in their entirety.

The present invention is directed towards a process for making a complexing agent with an en-antiomeric excess of at least 60%, wherein said process comprises the following steps:

(a) reacting an aqueous slurry of alanine with an enantiomeric excess of at least 60% with formaldehyde and hydrocyanic acid, thereby forming an aqueous solution of alanine-bisacetonitrile, (b) saponifying the alanine-bisacetonitrile from step (a) by combining the aqueous solution obtained in step (a) with an aqueous solution of alkali metal hydroxide.

Chelating agents such as methyl glycine diacetic acid (MGDA) and their respective alkali metal salts are useful sequestrants for alkaline earth metal ions such as $Ca^2$+ and $Mg^2$+. For that reason, they are recommended and used for various purposes such as laundry detergents and for automatic dishwashing (ADW) formulations, in particular for so-called phosphate-free laundry detergents and phosphate-free ADW formulations. For shipping such chelating agents, in most cases either solids such as granules are being applied or aqueous solutions.

Many processes have been developed to synthesise MGDA and its alkali metal salts. In many instances, such processes were developed in order to reduce the amount of impurities. For example, nitrilotriacetic acid (NTA) and its alkali metal salts are very undesirable as the are suspected to be cancerogenic.

In WO 2016/102494, a process is disclosed wherein an aqueous slurry of racemic alanine is reacted with hydrocyanic acid and formaldehyde. The resulting racemic alanine-bisacetonitrile ("D,L-ABAN") is then purified by crystallization. In addition, WO 2016/102494 discloses that said crystalline precursor has improved storage stability.

It is an objective of the present invention, though, to provide an improved process for making MGDA with high purity.

Accordingly, the process defined at the outset has been found, hereinafter also referred to as "inventive process". The inventive process comprises the steps of (a) reacting an aqueous slurry of alanine with an enantiomeric excess of at least 60% with formaldehyde and hydrocyanic acid, thereby forming an aqueous solution of alanine-bisacetonitrile, said step also being referred to as "step (a)", and (b) saponifying the alanine-bisacetonitrile from step (a) by combining the aqueous solution obtained in step (a) with an aqueous solution of alkali metal hydroxide, said step also being referred to as "step (b)".

Step (a) and step (b) are performed subsequently.

It was found that—although the inventive process is devoid of a crystallization step as disclosed in WO 2016/102494—MGDA and its alkali metal salts having excellent purity may be produced.

Steps (a) and (b) will be described in more detail below.

Step (a) starts off from alanine, for example D-alanine and L-alanine, with an enantiomeric excess of at least 60%, preferably at least 80% and up to enantiomerically pure alanine. Such alanine is general referred to as "said alanine". Preferably, alanine in step (a) is predominantly the L-isomer with an enantiomeric excess of at least 60%. Even more preferably, step (a) starts off from enantiomerically pure L-alanine or from L-alanine with an enantiomeric excess of 95 to 99.5%. The enantiomeric excess of alanine may be determined by polarimetry or by HPLC with a chiral column, for with an immobilized optically active ammonium salt such as D-penicillamine.

Preferably, in step (a), said alanine is provided mainly in zwitterionic form, thus neither as alkali metal salt nor as ammonium salt.

In step (a), said alanine is slurried in water. The weight ratio of alanine and water may be in the range of from 1:5 to 1:1, preferably 1:4 to 1:2.

The water used is preferably de-ionized, for example distilled or purified with the help of an ion exchanger. Preferably, such water has a calcium content of 0.01 mg/l or less and a Mg content of 0.01 mg/l or less.

In step (a) of the inventive process, a double Strecker synthesis is carried out by treating the aqueous slurry of said alanine with formaldehyde and hydrocyanic acid. Said addition of formaldehyde and hydrocyanic acid can be performed in one or more portions. Formaldehyde can be added as gas or as formalin solution or as paraformaldehyde. Preferred is the addition of formaldehyde as 30 to 35% by weight aqueous solution.

It is preferred to first add formaldehyde and then hydrocyanic acid.

In a particular embodiment of the present invention, step (a) of the inventive process is being carried out at a temperature in the range of from 20 to 80° C., preferably from 35 to 65° C.

In one embodiment of the present invention, step (a) of the inventive process is carried out at a constant temperature in the above range. In another embodiment, step (a) of the inventive process is being carried using a temperature profile, for example by starting the reaction at 40° C. and then stirring the reaction mixture at 50 to 60° C.

In one embodiment of the present invention, step (a) of the inventive process is carried out at elevated pressure, for example 1.01 to 6 bar. In another embodiment, step (a) of the inventive process is carried at normal pressure (1 bar).

Preferably, the pH value during step (a) is decreasing, and neither base nor acid other than HCN is added. In such embodiments, at the end of step (a), the pH value may have dropped to 2 to 4.

In one embodiment of step (a), about 2 moles formaldehyde and about 2 moles of HCN are added per mole of said alanine. In one embodiment of step (a), a stoichiometric amount or an excess of HCN is used, for example 2.00 or 2.01 to 2.05 mol of HCN per mole of alanine, and an undercut or stoichiometric amount of formaldehyde, for example 1.97 to 1.99 or 2.00 mol of formaldehyde per mole of alanine.

In another embodiment of the present invention, alanine is used in an excess, compared to HCN and formaldehyde, for example 1.97 to 1.99 mol of HCN and 1.95 to 1.99 mol of formaldehyde per mole of alanine.

Step (a) can be performed in any type of reaction vessel that allows the handling of hydrocyanic acid. Useful are, for example, flasks, stirred tank reactors and cascades of two or more stirred tank reactors.

During step (a) it can be observed that the precipitate of said alanine dissolves and partially reprecipitates. However, at the end of step (a), a clear aqueous solution has formed.

In one embodiment of the present invention, the duration of step (a) is in the range of from 30 minutes to 10 hours, preferably 40 minutes to 400 minutes, more preferably one hour to 200 minutes.

Step (b) includes saponifying the alanine-bisacetonitrile from step (a) by combining the aqueous solution obtained in step (a) with an aqueous solution of alkali metal hydroxide.

As alkali metal hydroxide, LiOH, NaOH, KOH, RbOH and CsOH may be applied. However, preferred are KOH and NaOH and combinations thereof, and even more preferred is NaOH.

In one embodiment of step (b), alanine-bisacetonitrile and alkali metal hydroxide are applied in a molar ratio of from 1:2.5 to 1:3.5, preferred 1:2.8 to 3.3.

In one embodiment of step (b), the aqueous solution of step (a) is added to an aqueous solution of alkali metal hydroxide.

In another embodiment of step (b), the aqueous solution of step (a) and a solution of alkali metal hydroxide are simultaneously added to an aqueous solution of alkali metal hydroxide.

In another embodiment of the present invention, the solution resulting from step (a) and an aqueous solution of alkali metal hydroxide are being added simultaneously to a vessel.

In a preferred embodiment of step (b), the dinitrile resulting from step (a) will be saponified in two steps (b1) and (b2) at different temperatures.

In one embodiment of the present invention, the alkali metal hydroxide in step (b) corresponds to an excess, referring to the nitrile group and neutralization of the carboxylic acid group of alanine.

In an alternative embodiment of the present invention, in step (b), the alkali metal hydroxide corresponds to an undercut, referring to the nitrile group and neutralization of the carboxylic acid group of alanine.

Different temperature means in the context of step (b) that the average temperature of step (b1) is different from the average temperature of step (b2). Preferably, step (b1) is being performed at a temperature lower than step (b2). Even more preferably, step (b2) is being performed at an average temperature that is at least 100° C. higher than the average temperature of step (b1).

For example, in one embodiment of the present invention, (b1) in the range of from 20 to 80° C., preferably 30 to 60° C., (b2) in the range of from 90 to 190° C.

It is possible to split any of steps (b1) and (b2) into sub-steps.

Step (b1) can be started by adding the solution resulting from step (a) to an aqueous solution of alkali metal hydroxide or to simultaneously add the aqueous solution of step (a) and a solution of alkali metal hydroxide to an aqueous solution of alkali metal hydroxide.

Step (c1) can be performed at a temperature in the range of from 20 to 80° C., preferably 30 to 60° C. In the context of step (b1) “temperature” refers to the average temperature.

As a result of step (b1), an aqueous solution of the respective diamide and its respective alkali metal salt may be obtained, M being alkali metal. Said solution may also contain L-MGDA and the corresponding monoamide and/or its mono- or dialkali metal salt.

Step (b2) may be performed at a temperature of from 90 to 190° C., preferably from 130 to 195° C., more preferably 175 to 195° C. In the context of step (b2) “temperature” refers to the average temperature.

In one embodiment of the present invention, step (b2) is split into two sub-steps, the first one being performed at a temperature in the range of from 90 to 110° C. and the second one of from 130 to 195° C., more preferably 175 to 195° C.

In one embodiment of the present invention, step (b2) has an average residence time in the range of from 5 to 180 minutes.

In preferred embodiments, the higher range of the temperature interval of step (b2) such as 190 to 195° C. is combined with a short residence time such as 20 to 25 minutes, or the lower range of the temperature interval of step (b2) such as 175 to 180° C. is combined with a longer residence time such as 50 to 60 minutes, or a middle temperature such as 185° C. is combined with a middle residence time such as 35 to 45 minutes.

Step (b2) can be performed in the same reactor as step (b1), or—in the case of a continuous process—in a different reactor.

In one embodiment of the present invention, step (b2) is carried out with an excess of base of 1.01 to 1.20 moles of hydroxide per mole of nitrile group.

Depending on the type of reactor in which step (b2) is performed, such as an ideal plug flow reactor, the average residence time can be replaced by the residence time.

In one embodiment of the present invention, step (b1) is carried out in a continuous stirred tank reactor and step (b2) is being carried out in a second continuous stirred tank reactor. In a preferred embodiment, step (b1) is being carried out in a continuous stirred tank reactor and step (b2) is being carried out in a sequence of a stirred tan reactor and a plug flow reactor, such as a tubular reactor.

In one embodiment of the present invention, step (b1) of the inventive process is being out at elevated pressure, for example at 1.05 to 6 bar. In another embodiment, step (b1) of the inventive process is being carried out at normal pressure.

Especially in embodiments wherein step (b2) is carried out in a plug flow reactor, step (b2) may be carried out at elevated pressure such as 1.5 to 40 bar, preferably at least 20 bar. The elevated pressure may be accomplished with the help of a pump or by autogenic pressure elevation.

Preferably, the pressure conditions of steps (b1) and (b2) are combined in the way that step (b2) is carried out at a higher pressure than step (b1).

During step (b2), a partial racemization takes place. Without wishing to be bound by any theory, it is likely that racemization takes place on the stage of the above L-diamide or of L-MGDA.

In one embodiment of the present invention, the inventive process may comprise steps other than steps (a) and (b) disclosed above. Such additional steps may be, for example, one or more decolourization steps, for example with activated carbon or with peroxide such as $H_2O_2$.

A further step other than step (a) or (b) that is preferably carried out after step (b2) is stripping with nitrogen or steam in order to remove ammonia. Said stripping can be carried out at temperatures in the range of from 90 to 110° C. By nitrogen or air stripping, water can be removed from the solution so obtained. Stripping is preferably carried out at a pressure below normal pressure, such as 650 to 950 mbar.

In embodiments wherein an inventive solution is desired, the solution obtained from step (b2) is just cooled down and, optionally, concentrated by partially removing the water. If dry samples of inventive mixtures are required, the water can be removed by spray drying or spray granulation.

The inventive process may be carried out as a batch process, or as a semi-continuous or continuous process.

By performing the inventive process, MGDA and its alkali metal salts are obtained in excellent purity.

The invention is further illustrated by working examples.

With exception of ee values, percentages in the context of the examples refer to percent by weight unless expressly indicated otherwise.

The expressions (±)-alanine and D,L-alanine are used interchangeably. The expressions D,L-MGDA and (±)-MGDA are used interchangeably.

The ee values were determined by HPLC using as column Chirex 3126; (D)-penicillamine, 5 μm, 250·4.6 mm. The mobile phase (eluent) was 0.5 M aqueous $CuSO_4$-solution. Injection: 5 μl, flow: 1.5 ml /min. Detection by UV light at 254 nm. Temperature: 20° C. Running time is 25 min.

I. EXAMPLE 1: SYNTHESIS OF D-MGDA-$Na_3$

I.1 Synthesis of an Aqueous Solution of D-Aban

A 2.5-litre stirred reactor was charged with 234 g of D-alanine (2.60 mol) and 480 g of deionized water. To the resultant slurry 520.3 g of formaldehyde (30.0% in water, 5.20 mol) were added at 25° C. over a time period of 10 minutes. The slurry did not show any significant temperature change during formaldehyde addition. After complete addition of formaldehyde, the temperature was raised to 40° C. Within 60 minutes, 142.0 g of hydrogen cyanide (99.0%, 5.20 mol) were added while keeping the temperature at 40° C. In the course of the HCN addition the white solid was completely dissolved, but during the second half of the HCN addition a white precipitate formation was observed again. At the end of the HCN addition, said white precipitate had dissolved completely. After complete addition of HCN the resultant solution was stirred at 40° C. for 60 minutes for completion of the reaction. During this stirring, no formation of solids was observed.

Analytics (HPLC): D-alanine-bisacetonitrile: 28.9 wt.-%, D-alanine mono-acetonitrile: 0.3 wt.-%, alanine: not detected

I.2 Synthesis of an Aqueous Solution of Complexing Agent D-Mgda-$Na_3$

A 2.5-litre stirred reactor was charged with 644.8 g of sodium hydroxide (50.0% in water, 8.06 mol). The obtained solution D-ABAN from step I.1 was dosed in the caustic solution during 60 minutes at a temperature of 60° C. After complete addition of the ABAN-solution the solution was stirred for 30 minutes at 60° C. Then, the reaction mixture was heated up to temperature 95 to 100° C. to finalize the saponification reaction. During this step the reactor was also charged with a continuous air flow to strip off the evolving ammonia. The aqueous solution was stirred for 240 minutes at this temperature level and then concentrated to 40% by weight (calculated on MGDA-$Na_3$).

Analytics: Fe-binding capacity (titration): 40.0 wt.-% (calc. as MGDA-$Na_3$); HPLC: NTA-$Na_3$: 0.04 wt.-%, ee-value: 97.6

I.3 Synthesis of an Aqueous Solution of L-Aban

The protocol of I.1 was followed but L-alanine was used as starting material. Accordingly, an aqueous solution of L-ABAN was obtained.

Analytics (HPLC): L-alanine-bisacetonitrile: 30.3 wt.-%, L-alanine-monoacetonitrile: 0.5 wt.-%, alanine: not detected

I.4 Synthesis of an Aqueous Solutions Of Complexing Agent L-Mgda-$Na_3$

The protocol of 1.2 was followed but the aqueous solution of L-ABAN from I.3 was used as starting material. Accordingly, a 40% by weight (calculated as MGDA-$Na_3$) aqueous solution of L-MGDA-$Na_3$ was obtained.

II. COMPARATIVE EXAMPLE 1: SYNTHESIS OF (±)-MGDA-$Na_3$

II.1 Synthesis of an Aqueous Solution of (±)-Aban

A 2.5-litre stirred reactor was charged with 234 g of (±)-alanine (2.60 mol) and 480 g of deionized water. To the resultant slurry 520.3 g of formaldehyde (30.0% in water, 5.20 mol) were dosed at 25° C. within 10 minutes. The white slurry did not show any significant temperature change during formaldehyde addition. After complete addition of the formaldehyde the temperature was raised to 40° C. Within 60 minutes, 142.0 g of hydrogen cyanide (99.0%. 5.20 mol) were added. The temperature was maintained at 40° C. In the course of the addition of HCN the white solid dissolved completely and no solid was formed during the remaining addition of HCN. After complete addition of HCN the solution was stirred at 40° C. for 60 minutes. During this completion of the reaction no precipitate formation was observed. At the end of the reaction, the vessel was flushed with a small amount of de-ionized water.

Analytics (HPLC): (±)-alanine-bisacetonitrile: 28.9 wt.-%, alanine mono-acetonitrile: 0.6 wt.-%, alanine: not detected

II.2 Synthesis of an Aqueous Solution of Complexing Agent (±)-Mgda-$Na_3$

The protocol of 1.2 was followed but the aqueous solution of (±)-ABAN from II.1 was used as starting material. Accordingly, a 40% by weight (calculated as MGDA-$Na_3$) aqueous solution of (±)-MGDA-$Na_3$ was obtained.

Analytics: Fe-binding capacity (titration): 40.1 wt.-% (calc. as MGDA-$Na_3$); HPLC: NTA-$Na_3$: 0.09 wt.-%, ee-value: 0.0

The invention claimed is:

1. A process for making a complexing agent wherein the complexing agent is methyl glycine diacetic acid (MGDA) with an enantiomeric excess of at least 60%, wherein said process comprises the following steps:

(a) in the absence of an alkali metal, reacting an aqueous slurry of alanine with an enantiomeric excess of at least 60% with formaldehyde and hydrocyanic acid by first adding the formaldehyde to the aqueous slurry followed by adding the hydrocyanic acid, thereby forming an aqueous solution of alanine-bisacetonitrile, and (b) saponifying the alanine-bisacetonitrile from step (a) by combining the aqueous solution obtained in step (a) with an aqueous solution of alkali metal hydroxide.

2. The process according to claim 1, wherein alanine in step (a) is predominantly the L-isomer with an enantiomeric excess of at least 60%.

3. The process according to claim 1, wherein in step (b), the aqueous solution of step (a) is added to an aqueous solution of alkali metal hydroxide.

4. The process according to claim 1, wherein the alkali metal hydroxide is sodium hydroxide.

5. The process according to claim 1, wherein step (b) is performed at two different temperatures, (b1) in the range of from 20 to 80° C., and (b2) in the range of from 90 to 190° C.

6. The process according to claim 1, wherein in step (b), the molar amount of alkali metal hydroxide corresponds to an excess, referring to the nitrile group and neutralization of the carboxylic acid group of alanine.

7. The process according to claim 1, wherein in step (b), alkali metal hydroxide corresponds to an undercut, referring to the nitrile group and neutralization of the carboxylic acid group of alanine.

* * * * *